United States Patent
Backer et al.

(10) Patent No.: US 6,384,256 B1
(45) Date of Patent: May 7, 2002

(54) PROCESS FOR THE PREPARATION OF SULFUR-CONTAINING ORGANOSILICON COMPOUNDS

(75) Inventors: Michael Wolfgang Backer, Vale of Glamorgan (GB); Howard Marvin Bank, Freeland, MI (US); John Michael Gohndrone, Midland, MI (US); William Charles Maki, Midland, MI (US); Charles Edmund Skinner, Midland, MI (US); Anil Kumar Tomar, Midland, MI (US); Hongjun Yue, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/895,720

(22) Filed: Jun. 29, 2001

(51) Int. Cl.$^7$ .................................................. C07F 2/08
(52) U.S. Cl. ..................................................... 556/427
(58) Field of Search ......................................... 556/427

(56) References Cited

U.S. PATENT DOCUMENTS

| | | | |
|---|---|---|---|
| 3,590,065 A | 6/1971 | Rakus et al. ............. | 260/448.8 |
| 4,082,790 A | 4/1978 | Speier ...................... | 260/448.8 |
| 4,401,826 A | 8/1983 | Selin ........................ | 556/429 |
| 4,556,724 A | 12/1985 | Seiler et al. ............... | 556/429 |
| 5,107,009 A | 4/1992 | Rauleder et al. ........... | 556/429 |
| 5,399,739 A | 3/1995 | French et al. .............. | 556/427 |
| 5,405,985 A | 4/1995 | Parker et al. .............. | 556/427 |
| 5,466,848 A | 11/1995 | Childress .................. | 556/427 |
| 5,468,893 A | 11/1995 | Parker et al. .............. | 556/427 |
| 5,489,701 A | 2/1996 | Childress et al. .......... | 556/427 |
| 5,583,245 A | 12/1996 | Parker et al. .............. | 556/427 |
| 5,596,116 A | 1/1997 | Childress et al. .......... | 556/427 |
| 5,663,396 A | 9/1997 | Musleve et al. ........... | 556/427 |
| 5,840,952 A | 11/1998 | Kudo et al. ................ | 556/429 |
| 5,859,275 A | 1/1999 | Munzenberg et al. ...... | 556/427 |
| 5,892,085 A | 4/1999 | Munzenberg et al. ...... | 552/427 |
| 5,936,112 A | 8/1999 | Gobel et al. ............... | 556/427 |
| 6,066,752 A | 5/2000 | Takata et al. .............. | 556/427 |
| 6,140,524 A | 10/2000 | Ichinohe et al. ........... | 556/427 |
| 6,172,251 B1 * | 1/2001 | Parker ....................... | 556/427 |
| 6,194,595 B1 * | 2/2001 | Michel et al. ............. | 556/427 |
| 6,274,755 B1 * | 8/2001 | Munzenberg et al. ...... | 556/427 |
| 6,294,683 B1 * | 9/2001 | Johnson et al. ............ | 556/427 |

* cited by examiner

Primary Examiner—Paul F. Shaver
(74) Attorney, Agent, or Firm—Alan Zombeck; Jennifer S. Warren

(57) ABSTRACT

A process for the production of organosilicon compounds of the formula:

$$(RO)_{3-m}R_mSi\text{-Alk-}S_n\text{-Alk-}SiR_m(OR)_{3-m}$$

where R is independently a monovalent hydrocarbon of 1 to 12 carbon atoms; Alk is a divalent hydrocarbon of 1 to 18 carbon atoms;
m is an integer of 0 to 2, n is a number from 1 to 10; is disclosed. The process comprises:

(A) reacting an alkali metal hydroxide compound, a sulfide compound having the formula $M_2S_n$ or MHS, where H is hydrogen, M is ammonium or an alkali metal, n is as defined above,
and sulfur in water to form a polysulfide mixture, (B) reacting said polysulfide mixture with a silane compound of the formula;

$$(RO)_{3-m}R_mSi\text{-Alk-X}$$

where X is Cl, Br or I, and m is the same as above, in the presence of a phase transfer catalyst. The process provides sulfur containing organosilicon compounds based on phase transfer catalysis techniques that result in a final product composition having greater stability, purity, and appearance. The process also minimizes or eliminates hydrogen sulfide as a side product.

42 Claims, No Drawings

PROCESS FOR THE PREPARATION OF SULFUR-CONTAINING ORGANOSILICON COMPOUNDS

FIELD OF THE INVENTION

This invention relates to a process for the production of sulfur containing organosilicon compounds by phase transfer catalysis techniques. The process involves first reacting an alkali metal hydroxide compound with a sulfide compound and sulfur in water to form a polysulfide mixture. The polysulfide mixture is then reacted with a silane compound in the presence of a phase transfer catalyst.

BACKGROUND OF THE INVENTION

Sulfur containing organosilicon compounds are useful as reactive coupling agents in a variety of commercial applications. In particular, sulfur containing organosilicon compounds have become essential components in the production of tires based on rubber vulcanates containing silica. The sulfur containing organosilicon compounds improve the physical properties of the rubber vulcanates containing silica resulting in automotive tires with improved abrasion resistance, rolling resistance, and wet skidding performance. The sulfur containing organosilicon compounds can be added directly to the rubber vulcanates containing silica, or alternately, can be used to pre-treat the silica prior to addition to the rubber vulcanate composition.

Numerous methods have been described in the art for the preparation of sulfur containing organosilicon compounds. For example, U.S. Pat. No. 5,399,739 by French et al. describes a method for making sulfur-containing organosilanes by reacting an alkali metal alcoholate with hydrogen sulfide to form an alkali metal hydrosulfide, which is subsequently reacted with an alkali metal to provide an alkali metal sulfide. The resulting alkali metal sulfide is then reacted with sulfur to provide an alkali metal polysulfide which is then finally reacted with a silane compound of the formula $X-R^2-Si(R^1)_3$, where X is either chlorine or bromine to produce the sulfur-containing organosilane.

U.S. Pat. Nos. 5,466,848, 5,596,116, and 5,489,701 describe processes for the preparation of silane polysulfides. The '848 patent process is based on first producing sodium sulfide by the reaction of hydrogen sulfide with sodium ethoxylate. The sodium sulfide is then reacted with sulfur to form the tetrasulfide, which is subsequently reacted with chloropropyltriethoxysilane to form 3,3'-bis (triethoxysilylpropyl) tetrasulfide. The '116 patent teaches a process for the preparation of polysulfides, without the use of hydrogen sulfide, by reacting a metal alkoxide in alcohol with elemental sulfur, or by reacting sodium metal with elemental sulfur and an alcohol, with a halohydrocarbylalkoxysilane such as chloropropyltriethoxysilane. The '701 patent claims a process for the preparation of silane polysulfides by contacting hydrogen sulfide gas with an active metal alkoxide solution and subsequently reacting the reaction product with a halohydrocarbylalkoxysilane such as chloropropyltriethoxysilane.

U.S. Pat. No. 5,892,085 describes a process for the preparation of high purity organosilicon disulphanes. U.S. Pat. No. 5,859,275 describes a process for the production of bis (silylorganyl) polysulphanes. Both the '085 and '275 patents describe anhydrous techniques involving the direct reaction of a haloalkoxysilane with a polysulphide.

U.S. Pat. No. 6,066,752 teaches a process for producing sulfur-containing organosilicon compounds by reacting sulfur, an alkali metal, and a halogenalkoyxsilane in the absence of a solvent or in the presence of an aprotic solvent.

Most recently, U.S. Pat. No. 6,140,524 describes a method for preparing short chain polysulfide silane mixtures of the formula $(RO)_3SiC_3H_6S_nC_3H_6Si(RO)_3$ having a distribution where n falls in the range of $2.2 \leq n \leq 2.8$. The '524 method reacts metal polysulfides, typically $Na_2S_n$ with a halogenopropyltrialkoxysilane having the formula $(RO)_3SiC_3H_6X$ wherein X is a halogen, in alcohol solvent.

Alternative processes for the preparation of sulfur-containing organosilanes have been taught in the art based on the use of phase transfer catalysis techniques. Phase transfer catalysis techniques overcome many of the practical problems associated with the aforementioned prior art processes for producing sulfur-containing organosilicon compounds. Many of these problems are related to the use of solvents. In particular, the use of ethyl alcohol can be problematic because of its low flash point. Additionally, it is difficult to obtain and maintain anhydrous conditions necessary in many of the aforementioned prior art processes on an industrial scale.

Phase transfer catalysis techniques for producing sulfur-containing organosilicon compounds are taught for example in U.S. Pat. Nos. 5,405,985, 5,663,396, 5,468,893, and 5,583,245. While these patents teach new processes for the preparation of sulfur containing organosilicon compounds using phase transfer catalysis, there still exist many practical problems with the use of phase transfer techniques at an industrial scale. For example, there is a need to control the reactivity of the phase transfer catalyst in the preparation of sulfur-containing organosilanes so as to provide efficient, yet safe reactions that can be performed on an industrial scale. Furthermore, there is a need to improve the final product stability, appearance and purity. In particular, the phase transfer catalysis process of the prior art results in final product compositions containing high quantities of un-reacted sulfur species. These un-reacted sulfur species can precipitate in stored products with time causing changes in product sulfide distribution.

The need to improve product quality is of particular importance when an alkali metal or ammonium hydrogen sulfide is used as a starting material in phase transfer catalysis techniques. In these reactions, dangerous and odorous hydrogen sulfide is produced in side reactions. Product compositions containing even minor amounts of hydrogen sulfide deter their use in large-scale industrial processes.

It is therefore an object of the present invention to provide an improved process for the production of sulfur containing organosilicon compounds based on phase transfer catalysis techniques.

It is a further object of the present invention to provide a process for producing sulfur containing organosilicon compounds based on phase transfer catalysis techniques that result in a final product composition of greater stability, purity, and appearance.

It is yet a further object of the present invention to provide a process for producing sulfur containing organosilicon compounds based on phase transfer techniques using a sulfide compound that minimizes or eliminates hydrogen sulfide as a side product.

It is still a further object of the present invention that provides a process for producing sulfur containing organosilicon compounds based on phase transfer techniques using starting materials that are less costly that conventional prior art methods and minimizes un-reacted side products.

SUMMARY OF THE INVENTION

The present invention provides a process for the production of sulfur containing organosilicon compounds by phase transfer catalysis techniques. The improvement of the present invention is characterized by reacting an alkali metal hydroxide compound with a sulfide compound and sulfur in water to form a polysulfide mixture, which is then reacted with a silane compound in the presence of a phase transfer catalyst.

DETAILED DESCRIPTION OF THE INVENTION

The present invention is a process for the production of organosilicon compounds of the formula:

$$(RO)_{3-m}R_mSi\text{-Alk-}S_n\text{-Alk-SiR}_m(OR)_{3-m}$$

where R is independently a monovalent hydrocarbon of 1 to 12 carbon atoms; Alk is a divalent hydrocarbon of 1 to 18 carbon atoms; m is an integer of 0 to 2, n is a number from 1 to 10;
comprising:
(A) reacting an alkali metal hydroxide compound, a sulfide compound having the formula $M_2S_n$ or MHS, where H is hydrogen, M is ammonium or an alkali metal,
n is as defined above,
and sulfur in water to form a polysulfide mixture,
(B) reacting said polysulfide mixture with a silane compound of the formula;

$$(RO)_{3-m}R_mSi\text{-Alk-X}$$

where X is Cl, Br or I, and m is the same as above, in the presence of a phase transfer catalyst.

Examples of sulfur containing organosilicon compounds which may be prepared in accordance with the present invention are described in U.S. Pat. Nos. 5,405,985, 5,663, 396, 5,468,893, and 5,583,245, which are hereby incorporated by reference. The preferred sulfur containing organosilicon compounds which are prepared in accordance with the present invention are the 3,3'-bis(trialkoxysilylpropyl) polysulfides. The most preferred compounds are 3,3'-bis (triethoxysilylpropyl) disulfide and 3,3'-bis (triethoxysilylpropyl) tetrasulfide.

The first step of the present invention involves the formation of a polysulfide mixture by reacting an alkali metal hydroxide compound, a sulfide compound and sulfur in water.

The alkali metal hydroxide compounds that can be used in the present invention are the hydroxide compounds of the Group I alkali metals, such as lithium hydroxide, sodium hydroxide, potassium hydroxide, rubidium hydroxide, and cesium hydroxide. The preferred metal hydroxide compound is sodium hydroxide.

Sulfide compounds of the formula $M_2S_n$ or MHS are used in the reaction step (A) of the process of the present invention, where M represents an alkali metal or ammonium group and H represents hydrogen. Representative alkali metals include lithium, potassium, sodium, rubidium, or cesium. Preferably M is sodium. Examples of the MHS compound include NaHS, KHS, and NH$_4$HS. When the sulfide compound is an MHS compound, NaHS is preferred. Specific examples of the NaHS compound include NaHS flakes (containing 71.5–74.5% NaHS) and NaHS liquors (containing 45–60% NaHS) from PPG of Pittsburgh, Pa. Specific examples of compounds of $M_2S_n$ include Na$_2$S, K$_2$S, Cs$_2$S, (NH$_4$)$_2$S, Na$_2$S$_2$, Na$_2$S$_3$, Na$_2$S$_4$, Na$_2$S$_6$, K$_2$S$_2$ K$_2$S$_3$, K$_2$S$_4$, K$_2$S$_6$, and (NH$_4$)$_2$S$_2$. Preferably the sulfide compound is Na$_2$S. A particular preferred sulfide compound is sodium sulfide flakes (containing 60–63% Na$_2$S) from PPG of Pittsburgh, Pa.

The sulfur used in the first step of the present invention is elemental sulfur. The type and form are not critical and can include those commonly used. An example of a suitable sulfur material is 100 mesh refined sulfur powder from Aldrich, Milwaukee Wis.

The amount of alkali metal hydroxide compound, alkali metal hydrogen sulfide compound and sulfur used in the process of the present invention can vary. Preferably the molar ratio of S/HS$^-$ ranges from 0.1 to 10. The molar ratio of S/HS$^-$ compound can be used to affect the final product distribution, that is the average value of n in the formula, $(RO)_{3-m}R_mSi\text{-Alk-}S_n\text{-Alk-SiR}_m(OR)_{3-m}$. When the average value of n is desired to be 4 in the product formula, $(RO)_{3-m}R_mSi\text{-Alk-}S_n\text{-Alk-SiR}_m(OR)_{3-m}$, the preferred range for the molar ratio of S/HS$^-$ compound is from 2.7 to 3.2. When the average value of n is desired to be 2 in the product formula, $(RO)_{3-m}R_mSi\text{-Alk-}S_n\text{-Alk-SiR}_m(OR)_{3-m}$, the preferred range for the ratio of sulfur/sulfide compound is from 0.8 to 1.2.

The amount of alkali metal hydroxide added to step (A) of the process of the present invention can be from 0.1 to 10 based on the molar ratio of the amount of sulfide compound used. Preferably the molar ratio of alkali metal hydroxide to sulfide compound is from 0.8 to 1.2, and most preferably from 0.95 to 1.05.

The amount of water used in step (A) of the present invention can vary. Generally, a sufficient amount of water is added to prevent precipitation of dialkali metal sulfides that are formed in the reaction of step (A). Optional ingredients can also be added to the water to enhance the reaction. For example, sodium chloride or other brine salts can be added.

The reaction step (A) involves mixing an alkali metal hydroxide compound, an alkali metal hydrogen sulfide compound, sulfur and water together in a reaction vessel. The reaction step (A) can be conducted at a variety of temperatures, but generally in the range of 20 to 100° C. Preferably, the reaction is conducted at a temperature ranging from 50 to 90° C. Generally, the first step can be conducted at various pressures, but preferably the first step reaction is conducted at atmospheric pressure. The time needed for the reaction of the first step to occur is not critical, but generally ranges from 5 to 30 minutes.

The second step of the process of the present invention involves reacting the polysulfide mixture with a silane compound of the formula;

$$(RO)_{3-m}R_mSi\text{-Alk-X}$$

R can independently be any hydrocarbon group containing 1 to 12 carbon atoms. Thus, examples of R include methyl, ethyl, propyl, butyl, isobutyl, cyclohexyl, or phenyl. Preferably, R is a methyl or ethyl group. In the formula $(RO)_{3-m}R_mSi\text{-Alk-X}$, m is an integer and can have a value from 0 to 2. Preferably, m is equal to 0. Alk is a divalent hydrocarbon group containing 1 to 18 carbons. Alk can be for example; ethylene, propylene, butylene, or isobutylene. Preferably Alk contains 2 to 4 carbons, and most preferably, Alk is a propylene group. X is a halogen atom selected from chlorine, bromine, or iodine. Preferably X is chlorine. Examples of silane compounds that may be used in the present invention include chloropropyl triethoxy silane, chloropropyl trimethoxy silane, chloroethyl triethoxy silane, chlorobutyl triethoxy silane, chloroisobutylmethyl diethoxy silane, chloroisobutylmethyl dimethoxy silane, chloropropyldimethyl ethoxy silane. Preferably, the silane compound of the present invention is chloropropyl triethoxy silane (CPTES).

The silane compound, $(RO)_{3-m}R_m$Si-Alk-X, can be reacted directly with the polysulfide mixture as described above, or alternatively, the silane compound can be dispersed in an organic solvent to form an organic phase. Representative examples of organic solvents include toluene, xylene, benzene, heptane, octane, decane, chlorobenzene and the like. When an organic solvent is used, the preferred organic solvent is toluene.

When conducting the reaction in step (B) of the present invention, preferably the silane compound is reacted directly with polysulfide mixture as described above.

The amount of the silane compound $(RO)_{3-m}R_m$Si-Alk-X used in the process of the present invention can vary. An example of a suitable range includes from 1/10 to 10/1 based on the molar amount of alkali metal hydrogen sulfide compound used. When the average value of n is desired to be 4 in the product formula, $(RO)_{3-m}R_m$Si-Alk-$S_n$-Alk-$SiR_m(OR)_{3-m}$, the silane compound $(RO)_{3-m}R_m$Si-Alk-X is generally used from 2.0 to 2.10 in molar excess of the alkali metal hydrogen sulfide compound, with a range of 2.01 to 2.06 being the most preferable. When the average value of n is desired to be 2 in the product formula, $(RO)_{3-m}R_m$Si-Alk-$S_n$-Alk-$SiR_m(OR)_{3-m}$, the silane compound $(RO)_{3-m}R_m$Si-Alk-X is preferably used from 1.8 to 2.1 in molar excess of the alkali metal hydrogen sulfide compound, with a range of 1.9 to 2.0 being the most preferable.

The phase transfer catalysts operable in the present invention are the quaternary onium cations. Preferred examples of the quaternary onium cations as phase transfer catalysts are described in U.S. Pat. No. 5,405,985, which is hereby incorporated by reference. Preferably, the quaternary onium cation is tetrabutyl ammonium bromide or tetrabutyl ammonium chloride. The most preferred quaternary onium salt is tetrabutyl ammonium bromide. A particularly preferred quaternary onium salt is tetrabutyl ammonium bromide (99%) from Aldrich Chemical of Milwaukee, Wis.

The amount of the phase transfer catalyst used in the process may vary. Preferably the amount of phase transfer catalyst is from 0.1 to 10 weight %, and most preferably from 0.5 to 2 weight % based on the amount of silane compound used.

The phase transfer catalyst may be added to the reaction at any time. Preferably, the phase transfer catalyst is added to the polysulfide mixture prior to step (B), reaction with the silane compound.

When conducting step (B) of the present invention, preferably the silane compound is added to the polysulfide mixture at such a rate so as to maintain a constant reaction temperature. The reaction of step (B) of the present invention can be conducted at a variety of temperatures, but generally is conducted in the range of 40–100° C. Preferably, the reaction is conducted at a temperature ranging from 65–95° C. Generally, the second step can be conducted at a various pressures, but preferably the second step reaction is conducted at atmospheric pressure. The time needed for the reaction of the second step to occur is not critical, but generally ranges from 5 minutes to 6 hours.

The reaction steps of the present invention can also be conducted in the presence of an aqueous phase containing a buffer. The buffer can be a single compound such as an alkali metal salt of a phosphate, a hydrogen phosphate, a dihydrogen phosphate, a carbonate, a hydrogen carbonate, or a borate, or combinations thereof. Examples of buffers include; $Na_3PO_4$, $Na_2HPO_4$, $NaH_2PO_4$, $Na_2CO_3$, $NaHCO_3$, and $NaB_4O_7$. Preferably, the buffer is selected from $Na_3PO_4$, $Na_2CO_3$, or $K_2CO_3$.

The amount of the buffer added to the aqueous phase can vary, but generally is added in molar amounts equal to or greater than the number of moles of $M_2S_n$ or MHS. Although not to be limited to any theory, the present inventors believe the addition of a buffer to the aqueous phase in the process to prepare sulfur containing organosilicon compounds using phase transfer catalysis helps to control the pH of the reaction medium, thereby affecting product formation and minimizing side reactions, such as the production of hydrogen sulfide. Thus, one embodiment of the present invention provides sulfur containing organosilicon compounds produced in the reaction described above by controlling the pH. The pH of the aqueous phase used in the reaction of the present invention can be controlled by the addition of a buffer, as described above, or alternatively, by the addition of any acidic or basic compounds at such a rate and concentration so as to maintain a pH during the reaction in the range of 7 to 14. The present inventors have also found that pH can have an influence on the product distribution, that is, the value of n in the product formula $(RO)_{3-m}R_m$Si-Alk-$S_n$-Alk-$SiR_m(OR)_{3-m}$. When the average value of n is desired to be 2 in the product formula, $(RO)_{3-m}R_m$Si-Alk-$S_n$-Alk-$SiR_m(OR)_{3-m}$, the preferred pH range is from 8 to 10. When the average value of n is desired to be 4 in the product formula, $(RO)_{3-m}R_m$Si-Alk-$S_n$-Alk-$SiR_m(OR)_{3-m}$, the preferred pH range is from 11 to 14.

In a preferred embodiment of the present invention, the alkali metal hydroxide, the sulfide compound, the phase transfer catalyst, water, and sulfur, are mixed together to form a polysulfide mixture. The polysulfide mixture is then reacted with the silane compound, $(RO)_{3-}R_m$Si-Alk-X, as described supra. This reaction can be conducted at a variety of temperatures, but generally in the range of 40–100° C. Preferably, the reaction is conducted at a temperature ranging from 65–95° C. Generally, the first step can be conducted at various pressures, but preferably the first step reaction is conducted at atmospheric pressure. The time needed for the reaction of the first step to occur is not critical, but generally ranges from 5 to 30 minutes. The intermediate reaction product is then reacted with the silane compound, $(RO)_{3-m}R_m$Si-Alk-X.

The amount of water used to create the aqueous phase or polysulfide mixture can vary, but is preferably based on the amount of the silane compound of the formula, $(RO)_{3-m}R_m$Si-Alk-X, used in the process. Water can be added directly, or indirectly, as some water may already be present in small amounts in other starting materials. For purposes of the present invention, it is preferable to calculate the total amount of water present, that is, accounting for all water added either directly or indirectly. Preferably, the total amount of water used to create the aqueous phase or the intermediate reaction product is 1 to 100 weight % of the silane compound used, with a range of 2.5 to 70 weight % being more preferred. Most preferred is a range of 20 to 40 weight % of water used for the intermediate reaction product based on the amount of silane compound used.

At the end of the reaction, a product mixture is produced containing an organic phase, an aqueous phase, and possibly precipitated solid materials than can include salts such as NaCl, $Na_2HPO_4$, or $NaHCO_3$ formed during the reaction. The organic phase contains the organosilane compound.

The present invention also encompasses processing steps to enhance the separation of the organosilane compound from the product mixture. This separation can be the phase separation of the organic and aqueous phase, resulting directly from the reaction of components (A), (B), and optional (C), as described above. Alternatively, if precipitated salts are formed during the reaction, the salts can be separated first by a filtering process or decanting method prior to the phase separation. Preferably, water or a dilute acidic solution is added to the product mixture prior to separation. The addition of water or a dilute acidic solution can enhance product quality during the phase separation by dissolving some or all of the precipitated salts. The amount of water or dilute acidic solution that is added during this step can vary from 10 to 50% based on the weight of the amount of silane compound used, preferably, the amount of water or dilute acidic solution added is from 20 to 40 weight % based on the amount of the silane compound used, and most preferably from 25 weight % to 35 weight %. When a dilute acidic solution is used, it can be any of the common acids, for example HCl, $HNO_3$, $H_2SO_4$, or the like, having a normal (N) concentration of 0.000001 to 5, preferably 0.01 to 1. The dilute acidic solution can also be prepared by the addition of a chlorosilane to water. Examples of chlorosilanes that can be used to create the dilute acidic solution include trichlorosilane, trichloromethylsilane, dimethyldichlorosilane, dimethylchlorosilane, trimethylchlorosilane . Preferably, 0.5 to 10 weight % chlorosilane can be used to prepare the dilute acidic solution, with 1 to 5 weight % being the most preferred. When a chlorosilane is used to create the dilute acidic solution, the chlorosilane is preferably trimethylchlorosilane.

Following the addition of water or a dilute acidic solution to the product mixture, the organosilicon compound is isolated from the product mixture by phase separating the organic phase and aqueous phase. The organic phase containing the organosilicon compound can be further subjected to a drying step. One example of the drying step can be to treat the organic phase under vacuum to remove any volatile organic materials present along with any residual water that may be present. This drying step can involve, for example, heating the organic phase to a temperature of 20 to 160° C. under a reduced pressure of 5 to 35 mm Hg (0.67 to 4.65 kPa), preferably the conditions are 90 to 120° C. at 5 to 25 mm Hg (0.67 to 3.33 kPa). Alternatively, the drying step of the organic phase can involve the use of a thin film stripper to remove volatile organics materials and residual water content in the organic phase. Yet another technique for the drying step of the organic phase can be to contact the organic phase containing the organosilicon compound with a desiccant material. The desiccant material can be any solid material known in the art to remove trace quantities of water in organic phases. These include known ionic hygroscopic materials like sodium sulfate, magnesium sulfate, and the like, or silicate based materials such as zeolites, silica, aluminasilicates, and the like. The preferred desiccant material is either sodium sulfate or magnesium sulfate, with sodium sulfate being the most preferred.

The dried organic phase can be subjected to additional steps according to the present invention that result in further improvements of the organosilicon compound final purity and appearance. The organic phase containing the organosilicon compound can be cooled to a temperature below 15° C. This cooling step results in the precipitation of un-reacted sulfur and sulfur compounds. Preferably, the organic phase containing the organosilicon compound is cooled to a temperature in the range of −20 to 30° C., and most preferably to a temperature in the range of −15 and 15° C. The precipitated unreacted sulfur and sulfur compounds can then be separated, for example by filtration, from the organic phase containing the organosilicon compound. The present inventors have found that removing un-reacted sulfur and sulfur compounds minimizes or eliminates further precipitation of sulfur and un-reacted sulfur compounds with time. As a result, the long-term storage stability of the organosilicon compound is enhanced by producing a composition that does not change with time or result in a product composition containing solid precipitates.

The following examples are provided to illustrate the present invention. These examples are not intended to limit the scope of the claims herein.

EXAMPLES

The distribution of the various sulfur containing organosilicon compounds were analyzed by high-pressure liquid chromatography (HPLC). Typical run conditions for HPLC analysis were as follows: 8–9 drops of the reaction sample were diluted in 8.5 g of cyclohexane, which was then filtered through a 0.2$\mu$m PTFE membrane (e.g. PURADISC™ 25TF of Whatman®) into a vial, a 10 $\mu$l sample of the filtrate was injected via an autosampler into a HPLC system (e.g. Hewlett-Packard 1050). The sample was fractionated on a Lichrosorp RP18 column (e.g. Ailtech Assoc., Inc; 250 mm×4.6 mm, 10$\mu$m) using a mixture of 96% acetonitrile and 4% tetrahydrofurane (vol/vol) as mobile phase. The fractions were investigated via UV-absorption detector using 254 nm as the appropriate excitation wavelength. Different UV-sensitivities of every single sulfide species were averaged by division of the respective peak area through specific, empirically evaluated, response factors* (RF) listed below that reflect the hyperchromy with every sulfur atom in the chain and elemental sulfur.

| HPLC Response Factors. | | | | | | | | | |
| --- | --- | --- | --- | --- | --- | --- | --- | --- | --- |
| S2 | S3 | S4 | S5 | S6 | S7 | S8 | S9 | S10 | $S_{elem.}$ |
| 1.0 | 3.52 | 6.39 | 9.78 | 13.04 | 17.39 | 20.87 | 26.08 | 31.30 | 37.26 |

*As reported by H.-D. Luginsland, "Reactivity of the Sulfur Functions of the Disulfane Silane TESPD and the Tetrasulfane Silane TESPT"; Rubber Division, American Chemical Society; Chicago, Ill., Apr. 13–16, 1999.

Example 1

A 1 L reactor, equipped with mechanical stirrer, 1 baffle, dropping funnel and internal thermometer, was loaded at 75 degrees Celsius with 114.02 g of an aqueous solution of sodium hydrogen sulfide (0.24% $Na_2S$, 45.77% NaHS), 51.00 g of water and 77.24 g of an aqueous solution of sodium hydroxide (48.20% NaOH). Then, 89.88 g of sulfur were added in portions, and the mixture was vigorously stirred until all solids were dissolved. Then, 14.40 g of a 25% aqueous catalyst solution (3.60 g of tetrabutyl ammonium bromide, TBAB, in 10.80 g of water) were added. Then 463.50 g of chloropropyltriethoxysilane were added quickly to keep the reaction temperature below 85 degrees Celsius. After the decrease of the exotherm, the mixture was stirred at a temperature level of 80 degrees Celsius, and the reaction progress was followed by quantitative gas chromatography analysis until chloropropyltriethoxysilane (CPTES) had reached a stable level after 3.5 hours. The reaction mixture was cooled to 50 degrees Celsius, then 131.10 g of water were carefully added until the formed sodium chloride precipitate was completely dissolved. The agitation was stopped and 446.30 g of aqueous phase were removed. Then, 6.18 g of ethanol and remaining water were evaporated out of the organic phase under vacuum conditions 25 mm Hg (3.33 kPa) and 50 degrees Celsius within 30 minutes with an air purge of 250 mL per minute. The remaining solution was cooled to 15 degrees Celsius, drained off (485.43 g raw material) and filtered in a Büchner funnel through Paper (e.g. Whatman® 1) and filter aid (e.g. Celite® 545 of ManCel Assoc., Inc.). For removal of remaining water droplets, 5.00 g of magnesium sulfate were added. The organic phase was filtered and 468.68 g of a clear, light amber liquid were received (Yield: 94.1% based on sulfide species). HPLC analysis showed an average sulfur rank of 3.81.

Example 2

A 1 L reactor, equipped with mechanical stirrer, 1 baffle, dropping funnel and internal thermometer, was loaded at 77 degrees Celsius with 114.02 g of an aqueous solution of sodium hydrogen sulfide (0.24% $Na_2S$, 45.77% NaHS), 51.0 g of water and 69.52 g of an aqueous solution of sodium hydroxide (48.2% NaOH). Then, 89.88 g of sulfur were added in portions, and the mixture was vigorously stirred until all solids were dissolved. Then, 14.40 g of a 25% aqueous catalyst solution (3.60 g of tetrabutyl ammonium bromide in 10.80 g of water) were added. Then 463.50 g of chloropropyltriethoxysilane were added quickly to keep the reaction temperature below 85 degrees Celsius. After the decrease of the exotherm, the mixture was stirred at a temperature of 80 degrees Celsius, and the reaction progress was followed by quantitative gas chromatography analysis until chloropropyltriethoxysilane had reached a stable level after 3.5 hours. The reaction mixture was cooled down to 50 degrees Celsius, then 127.46 g of water were carefully added until the formed sodium chloride precipitate was completely dissolved. The agitation was stopped and 400.16 g of aqueous phase were removed. Then, 5.83 g of ethanol and remaining water were evaporated out of the organic phase under vacuum conditions, 25 mm Hg (3.33 kPa), 50 degrees Celsius within 30 minutes with an air purge of 250 mL per minute. The remaining solution was cooled to 15 degrees Celsius, drained off (509.01 g raw material) and filtered in a Büchner funnel through Paper (e.g. Whatman® 1) and filter aid (e.g. Celite® 545 of ManCel Assoc., Inc.). For removal of remaining water droplets, 6.69 g of magnesium sulfate were added. The organic phase was filtered and 486.37 g of a clear, light amber liquid were received (Yield: 97.6% of theory based on sulfide species). HPLC analysis showed an average sulfur rank of 3.83.

Example 3

A 1-1-reactor, equipped with mechanical stirrer, 1 baffle, dropping funnel and internal thermometer, was loaded at 76 degrees Celsius with 114.02 g of an aqueous solution of sodium hydrogen sulfide (0.24% $Na_2S$, 45.77% NaHS), 51.00 g of water and 84.96 g of an aqueous solution of sodium hydroxide (48.2% NaOH). Then, 89.88 g of sulfur were added in portions, and the mixture was vigorously stirred until all solids were dissolved. Then, 14.4 g of a 25% aqueous catalyst solution (3.6 g of tetrabutyl ammonium bromide in 10.8 g of water) were added. Then 463.50 g of chloropropyltriethoxysilane were added quickly to keep the reaction temperature below 85 degrees Celsius. After the decrease of the exotherm, the mixture was stirred at a temperature level of 80 degrees Celsius, and the reaction progress was followed by quantitative gas chromatography analysis until chloropropyltriethoxysilane had reached a stable ratio level after 3.5 hours. The reaction mixture was cooled down to 50 degrees Celsius, then 131.22 g of water were carefully added until the formed sodium chloride precipitate was completely dissolved. The agitation was stopped and 419.48 g of aqueous phase were removed. Then, 9.06 g of ethanol and remaining water were evaporated out of the organic phase under vacuum conditions, 32 mm Hg (4.5 kPa), 50 degrees Celsius within 30 minutes with an air purge of 250 mL per minute. The remaining solution was cooled to 15 degrees Celsius, drained off (495.49 g raw material) and filtered in a Büchner funnel through Paper (e.g. Whatman® 1) and filter aid (e.g. Celite® 545 of ManCel Assoc., Inc.). For removal of remaining water droplets, 3.10 g of magnesium sulfate were added. The organic phase was filtered and 469.86 g of a clear amber liquid were received (Yield: 94.8% of theory based on sulfide species). HPLC analysis showed an average sulfur rank of 3.74.

Example 4

A 1 L reactor, equipped with mechanical stirrer, 1 baffle, dropping funnel and internal thermometer, was loaded at 78 degrees Celsius with 114.02 g of an aqueous solution of sodium hydrogen sulfide (0.24% $Na_2S$, 45.77% NaHS), 51.00 g of water and 77.24 g of an aqueous solution of sodium hydroxide (48.2% NaOH). Then, 86.88 g of sulfur were added in portions, and the mixture was vigorously stirred until all solids were dissolved. Then, 14.40 g of a 25% aqueous catalyst solution (3.60 g of tetrabutyl ammonium bromide in 10.80 g of water) were added. Then 459.00 g of chloropropyltriethoxysilane were added quickly to keep the reaction temperature below 152 85 degrees Celsius. After the decrease of the exotherm, the mixture was stirred at a temperature level of 80 degrees Celsius, and the reaction progress was followed by quantitative gas chromatography analysis until chloropropyltriethoxysilane had reached a stable ratio level after 3.5 hours. The reaction mixture was cooled to 50 degrees Celsius, then 131.10 g of water were carefully added until the formed sodium chloride precipitate was completely dissolved. The agitation was stopped and 418.97 g of aqueous phase were removed. Then, 6.57 g of ethanol and remaining water were evaporated out of the organic phase under vacuum conditions, 34 mm Hg (3.34 kPa), 50 degrees Celsius within 30 minutes with an air purge of 250 mL per minute. The remaining solution was cooled to 15 degrees Celsius, drained off (492.44 g raw material) and filtered in a Büchner funnel through Paper (e.g. Whatman® 1) and filter aid (e.g. Celite® 545 of ManCel Assoc., Inc.). For removal of remaining water droplets, 5.00 g of magnesium sulfate were added. The organic phase was filtered and 472.91 g of a clear, light amber liquid were received (Yield: 91.7% of theory based on sulfide species). HPLC analysis shows an averaged sulfur rank of 3.75.

Example 5

A reactor was charged with 50.0 g (0.589 mole) NaHS flakes, 56.6 g (1.767 mole) sulfur and 75.62 g water and mixed at room temperature. Then, 25.12 g (0.628 mole) NaOH pellets (NaOH/NaHS ratio=1.0 and S/NaHS ratio= 3.0) was charged quickly to prevent $H_2S$ formation and heated to 70° C. while mixing. The solution became clear yellowish red in 30 minutes when sulfur dissolved completely. No gas evolution was observed after the NaOH addition. A phase transfer catalyst, 25.0 wt % tetrabutyl ammonium bromide (TBAB) solution (4.54 g, 0.014 mole) was added to the sulfide aqueous phase and mixed for 15 minutes. Dark reddish black precipitates formed at the surface. Then, 302,5 g (1.256 mole) chloropropyltriethoxysilane (CPTES) was added slowly and reacted for 2 hours. The reaction mixture was cooled to 50° C. and the byproduct NaCl salt was dissolved in deionized water. The mixture was then phase separated. The organic phase (product) was filtered and analyzed by gas chromatography (GC) and high-pressure liquid chromatography (HPLC) techniques. HPLC analysis shows an averaged sulfur rank of 4.08.

A stable sulfide distribution was achieved in the initial stage of the reaction. No mercaptosilane was formed and no solid sulfur precipitation was observed on cooling and long-term storage of the product.

Example 6

A reactor was charged with 100 g (0.8316 mole) NaHS solution and heated to 50° C. Then, 66.5 g (0.8316 mole) of a 50 wt % NaOH solution (NaOH/NaHS ratio=1.0 and S/NaHS ratio=3.0) was added slowly and mixed. Solid crystals of $Na_2S$ formed and dispersed in aqueous phase. 79.3 g (2.495 mole) sulfur was added and mixed for 15 minutes at 83° C. Most of precipitates dissolved with the formation of $Na_2S$. Then, 4.0 g (0.013 mole) TBAB was added at 70° C. followed by addition of CPTES (402.0 g, 1.672 mole). No exotherm was observed during CPTES addition but an exotherm of 20° C. (70° to 90° C.) was observed after the CPTES addition for 7 minutes. Reaction was continued for 210 minutes before NaCl salt was dissolved in 177.4 g water at 30° C. After phase separation, 433.4 g organic phase (product) and 379.4 g. aqueous phase was collected. HPLC analysis showed an averaged sulfur rank of 3.86.

The GC data showed that the reaction was complete in 2 hours and the CPTES content was less than 1.0 wt %. There was no mercaptan compounds formed at any stage of the reaction in this process because of the use of sodium hydroxide, which kept the pH greater than 12. The HPLC data showed that there was no significant change in sulfide distribution as the reaction progressed; therefore a stable sulfide distribution was formed in the aqueous phase in the presence of sodium hydroxide.

Example 7

In this experiment the molar ratio of NaOH/NaHS was changed to 3.0. The reactor was charged with 37.7 g (0.942 moles) NaOH pallets and dissolved in 75.6 g water by stirring at 200 rpm. The temperature rose to 40° C. due to exothern. Then, 25.0 g (0.314 moles Na) NaHS flakes (containing 61.7% NaHS and 6.07% $Na_2S$, PPG) and 70.5 g (2.19 moles, S/HS$^-$ ratio7.0) sulfur were added slowly while mixing. A dark orange-red solution formed quickly with a slight evolution of gas. TBAB catalyst (4.5 g, 0.014 moles) was added at 68° C. to the polysulfide aqueous phase and mixed for 10 minutes. Chloropropyltriethoxysilane (302.5 g, 1.2562 moles CPTES) was added slowly and reacted for 1.5 hour at 80–85° C. An exotherm of 17° C. was observed during CPTES addition. The reaction mixture was cooled to 50° C. and salt was dissolved in water. Upon phase separation 252.8 g aqueous phase and 309.1 g amber organic phase was obtained. The organic phase was analyzed by HPLC for sulfur distribution and an average sulfur rank was 3.93. The HPLC results showed the sulfide distribution equivalent to example 6, however, the GC showed ~15 wt % unreacted CPTES. Yellow sulfur also precipitated from the product overnight.

Example 8

Another experiment on equivalent molar amount of NaOH and NaHS and three molar times of sulfur is provided in this example. First, 50.0 g (0.6281 mole) NaHS flakes, 25.12 g (0.6281 mole) NaOH pallets and 60.42 g (1.8844 mole) sulfur were charged in a 1 l. reactor at room temperature. Then, 75.62 g water was added slowly with continuous mixing. The reaction mixture was heated to 68° C. before adding 4.53 g TBAB catalyst as 25-wt % solutions. CPTES 317.61 g (1.32 mole) was added to the aqueous phase slowly to control the exotherm and reacted for 2 hour at 80–85° C. The byproduct NaCl salt was dissolved at 45° C. after the reaction was complete. After phase separation 316.93 g product was collected and analyzed by GC and HPLC. The sulfur rank calculated was 3.89. The GC showed 6.0 wt % unreacted CPTES because excess CPTES was used in the reaction. The product was light yellow-orange and clear.

Example 9 (comparative example)

3,3'-bis(triethoxysilylpropyl) tetrasulfide was also prepared from di-sodium sulfide as a starting material without sodium hydroxide. 81.0 g (0.623–moles) $Na_2S$ from PPG as 60 wt % active flakes, 59.92 g (1.187 moles) sulfur and 75.0 g deionized water were charged in a 1 l. reactor at room temperature. The mixture was heated to 68° C. while mixing at 300 rpm. All the solids dissolved in the solution after 15 minutes. Then, 2.4 g (0.0074 moles) TBAB as a 25-wt % solution was added and mixed for 10 minutes. Then, 300.0 g (1.246 moles) CPTES was added slowly and reacted for 120 minutes. The GC results showed less than 0.5 wt % unreacted CPTES. The salt was dissolved at 50° C. and the organic phase was phase separated. 274.8 g dark red-orange product was collected. The product was also analyzed by HPLC and sulfur rank was calculated to be 3.83. The product obtained from this method was darker in color and solids precipitated on cooling.

What is claimed is:

1. A process for the production of organosilicon compounds of the formula:

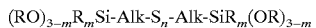

$(RO)_{3-m}R_mSi\text{-Alk-}S_n\text{-Alk-}SiR_m(OR)_{3-m}$ where R is independently a monovalent hydrocarbon of 1 to 12 carbon atoms; Alk is a divalent hydrocarbon of 1 to 18 carbon atoms;
m is an integer of O to 2, n is a number from 1 to 10;
comprising:
(A) reacting an alkali metal hydroxide compound, a sulfide compound having the formula $M_2S_n$ or MHS, where H is hydrogen, M is ammonium or an alkali metal,
n is as defined above,
and sulfur in water to form a polysulfide mixture,
(B) reacting said polysulfide mixture with a silane compound of the formula;

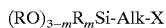

$(RO)_{3-m}R_mSi\text{-Alk-X}$ where X is Cl, Br or I, and m is the same as above, in the presence of a phase transfer catalyst.

2. The process of claim 1 wherein the alkali metal hydroxide is lithium hydroxide, potassium hydroxide, or sodium hydroxide.

3. The process of claim 2 wherein the alkali metal hydroxide is sodium hydroxide.

4. The process of claim 1 wherein the molar ratio of alkali metal hydroxide to sulfide compound 0.1 to 10.

5. The process of claim 4 wherein the molar ratio of alkali metal hydroxide to sulfide compound 0.8 to 1.2.

6. The process of claim 1 wherein the sulfide compound is selected from the group consisting of $Na_2S$, $K_2S$, $Cs_2S$, $(NH_4)_2S$, $Na_2S_2$, $Na_2S_3$, $Na_2S_4$, $Na_2S_6$, $K_2S_2$ $K_2S_3$, $K_2S_4$, $K_2S_6$, and $(NH_4)_2S_2$.

7. The process of claim 6 wherein the sulfide compound is $Na_2S$.

8. The process of claim 1 wherein the sulfide compound is selected from the group consisting of NaHS, KHS, and $NH_4HS$.

9. The process of claim 8 wherein the sulfide compound is NaHS.

10. The process of claim 1 wherein the molar ratio of sulfur to the sulfide compound is 0.1 to 10.

11. The process of claim 10 wherein the molar ratio of sulfur to the sulfide compound is 1.0 to 1.6.

12. The process of claim 10 wherein the molar ratio of sulfur to the sulfide compound is 2.7 to 3.2.

13. The process of claim 1 wherein the silane compound is selected from the group consisting of chloropropyl triethoxy silane, chloropropyl trimethoxy silane, chloroethyl triethoxy silane, chlorobutyl triethoxy silane, chloroisobutylmethyl diethoxy silane, chloroisobutylmethyl dimethoxy silane, and chloropropyldimethyl ethoxy silane.

14. The process of claim 13 wherein the silane compound is chloropropyl triethoxy silane.

15. The process of claim 1 wherein there is a 2.0 to 2.1 molar excess of the $(RO)_{3-m}R_mSi$-Alk-X silane compound to the sulfide compound.

16. The process of claim 1 wherein the phase transfer catalyst is a quaternary onium salt.

17. The process of claim 16 wherein the phase transfer catalyst is tetrabutyl ammonium bromide.

18. The process of claim 1 wherein the weight percent of the phase transfer catalyst to the silane compound is 0.1 to 10%.

19. The process of claim 18 wherein the weight percent of the phase transfer catalyst to the silane compound is 0.5 to 3%.

20. The process of claim 1 wherein the phase transfer catalyst is added in step (A).

21. A process for the production of organosilicon compounds of the formula:

$$(RO)_{3-m}R_mSi\text{-Alk-}S_n\text{-Alk-}SiR_m(OR)_{3-m}$$

where R is independently a monovalent hydrocarbon of 1 to 12 carbon atoms; Alk is a divalent hydrocarbon of 1 to 18 carbon atoms;

m is an integer of 0 to 2, n is a number from 1 to 10; comprising:

(A) reacting an alkali metal hydroxide compound with a sulfide compound having the formula $M_2S_n$ or MHS, where H is hydrogen, M is ammonium or an alkali metal, n is as defined above, in water to form a dialkali metal sulfide mixture, (B) reacting said dialkali metal sulfide mixture with sulfur to form a polysulfide mixture, (C) reacting said polysulfide mixture with a silane compound of the formula;

$$(RO)_{3-m}R_mSi\text{-Alk-X}$$

where X is Cl, Br or I, and m is the same as above, in the presence of a phase transfer catalyst.

22. A process for the production of organosilicon compounds of the formula:

$$(RO)_{3-m}R_mSi\text{-Alk-}S_n\text{-Alk-}SiR_m(OR)_{3-m}$$

where R is independently a monovalent hydrocarbon of 1 to 12 carbon atoms; Alk is a divalent hydrocarbon of 1 to 18 carbon atoms;

m is an integer of 0 to 2, n is a number from 1 to 10; comprising:

(A) reacting an alkali metal hydroxide compound, a sulfide compound having the formula $M_2S_n$ or MHS, where H is hydrogen, M is ammonium or an alkali metal, n is as defined above, and sulfur in water to form a polysulfide mixture, (B) reacting said polysulfide mixture with a silane compound of the formula;

$$(RO)_{3-m}R_mSi\text{-Alk-X}$$

where X is Cl, Br or I, and m is the same as above, in the presence of a phase transfer catalyst and an aqueous phase containing a buffer.

23. The process of claim 22 wherein the buffer is an alkali metal salt of a phosphate, a hydrogen phosphate, a dihydrogen phosphate, a carbonate, a hydrogen carbonate, or a borate.

24. The process of claim 23 wherein the buffer is selected from $Na_3PO_4$, $Na_2HPO_4$, $NaH_2PO_4$, $Na_2CO_3$, $NaHCO_3$, $K_2CO_3$, or $NaB_4O_7$.

25. The process of claim 24 wherein the buffer is $Na_3PO_4$.

26. The process of claim 24 wherein the buffer is $Na_2CO_3$.

27. The process of claim 24 wherein the buffer is $K_2CO_3$.

28. The process of claim 22 wherein the molar concentration of buffer in the aqueous phase is at least equal to the number of moles of $M_2S_n$ or MHS present.

29. The process of claim 22 wherein the phase transfer catalyst and the buffer are added in step (A).

30. A process for the production of organosilicon compounds of the formula:

$$(RO)_{3-m}R_mSi\text{-Alk-}S_n\text{-Alk-}SiR_m(OR)_{3-m}$$

where R is independently a monovalent hydrocarbon of 1 to 12 carbon atoms; Alk is a divalent hydrocarbon of 1 to 18 carbon atoms;

m is an integer of 0 to 2, n is a number from 1 to 10; comprising:

(A) reacting an alkali metal hydroxide compound, a sulfide compound having the formula $M_2S_n$ or MHS, where H is hydrogen, M is ammonium or an alkali metal, n is as defined above, and sulfur in water to form a polysulfide mixture, (B) reacting said polysulfide mixture with a silane compound of the formula;

$$(RO)_{3-m}R_mSi\text{-Alk-X}$$

where X is Cl, Br or I, and m is the same as above, in the presence of a phase transfer catalyst and an aqueous phase containing a buffer to form a product mixture, and (C) separating the organosilicon compound from the product mixture.

31. The process of claim 30 wherein the organosilicon compound is separated from the product mixture by (D) adding water or a dilute acidic solution to the product mixture, and (E) phase separating the product mixture into an organic phase containing the organosilicon compound and an aqueous phase.

32. The process of claim 31 wherein the weight percentage of water or dilute acidic solution to the silane compound is 10–50%.

33. The process of claim 31 wherein the weight percentage of water or dilute acidic solution to the silane compound is 20–40%.

34. The process of claim 30 wherein the organic phase containing the organosilicon compound is dried.

35. The process of claim 34 wherein the organic phase containing the organosilicon compound is dried by heating the organic phase at reduced pressures.

36. The process of claim 34 wherein the organic phase containing the organosilicon compound is dried by contacting the organic phase with a solid desiccant.

37. The process of claim 36 wherein the solid desiccant is sodium sulfate or magnesium sulfate.

38. The process of claim 37 wherein the desiccant is sodium sulfate.

39. The process of claim 30 further comprising the steps;

(F) cooling the organic phase containing the organosilicon compound below 15° C. to precipitate un-reacted sulfur compounds, (G) separating the organic phase containing the organosilicon compound from the precipitated un-reacted sulfur compounds.

40. The process of claim 39 wherein the organic phase containing the organosilicon compound is cooled to a temperature in the range of –20 to 30° C.

41. The process of claim 39 wherein the organic phase containing the organosilicon compound is cooled to a temperature in the range of –15 to 15° C.

42. The process of claim 30 wherein the phase transfer catalyst and the buffer are added in step (A).

* * * * *